United States Patent [19]

Stutz, Jr.

[11] Patent Number: 4,764,132
[45] Date of Patent: Aug. 16, 1988

[54] PACEMAKER CONNECTOR BLOCK FOR PROXIMAL RING ELECTRODE

[75] Inventor: William H. Stutz, Jr., Burbank, Calif.

[73] Assignee: Siemens-Pacesetter, Inc., Sylmar, Calif.

[21] Appl. No.: 58,684

[22] Filed: Jun. 3, 1987

Related U.S. Application Data

[63] Continuation of Ser. No. 845,288, Mar. 28, 1986, abandoned.

[51] Int. Cl.⁴ .............................................. H01R 4/36
[52] U.S. Cl. ................................. 439/810; 439/815; 439/843; 128/784
[58] Field of Search ............... 439/793, 810, 811, 812, 439/813, 814, 802, 840–859, 815; 128/784, 785, 786

[56] References Cited

U.S. PATENT DOCUMENTS

| | | | |
|---|---|---|---|
| 2,068,152 | 1/1937 | Rowe | 339/272 R |
| 3,086,190 | 4/1963 | Neidecker et al. | 339/258 A |
| 3,125,397 | 3/1964 | McGrath | 339/272 R |
| 3,205,474 | 9/1965 | Culver | 339/256 R |
| 3,292,138 | 12/1966 | Jones et al. | 339/258 A |
| 3,371,308 | 2/1968 | Maston | 339/256 R |
| 3,836,941 | 9/1974 | Izraeli | 339/272 R |
| 3,908,668 | 9/1975 | Bolduc | 339/272 R |
| 4,103,986 | 8/1978 | Izraeli | 339/272 UC |
| 4,387,727 | 6/1983 | Sandstrom | 339/177 R |
| 4,466,690 | 8/1984 | Osypka | 339/256 S |
| 4,570,642 | 2/1986 | Kane et al. | 128/785 |

FOREIGN PATENT DOCUMENTS 697756  9/1953  United Kingdom ............ 339/272 R

Primary Examiner—David Pirlot
Attorney, Agent, or Firm—Bryant R. Gold

[57] ABSTRACT

A connector block assembly for electrically connecting a proximal ring electrode of a bipolar pacemaker lead to the pacemaker. The connection is made in a way that maintains secure electrical contact and that prevents the delicate proximal ring electrode from being damaged or deformed. The pacemaker includes a connector block having a channel therethrough into which the proximal ring electrode is inserted. A C-ring is sandwiched between the ring electrode and an inner wall of the connector block's receiving channel. A setscrew adjustably forces the C-ring against the ring electrode. Mechanical stop means limit the transverse movement of the C-ring, thereby preventing the ring electrode from being deformed, while still maintaining a firm grasp of the ring electrode between the C-ring and the connector block. An alternative embodiment employs a resilient spring to firmly hold the ring electrode in electrical contact with the connector block.

5 Claims, 2 Drawing Sheets

PACEMAKER CONNECTOR BLOCK FOR PROXIMAL RING ELECTRODE

This is a continuation of co-pending application Ser. No. 845,288 filed on 3-28-86 now abandoned.

BACKGROUND OF THE INVENTION

The present invention relates to connector blocks used within connectors of implantable pacemakers. More particularly, the present invention relates to a connector block and method of attachment thereto which secures electrical contact with the proximal ring electrode of a bipolar pacing lead in a manner that prevents the proximal ring electrode from being damaged or deformed.

It is common practice in the pacemaker art to employ pacemaker leads that include two separate connectors. Such two-conductor leads are referred to in the art as "bipolar" leads. (Bipolar leads are usually realized with helically-wound coaxial conductors, one inside the other, with a layer of insulating material therebetween. However, the invention described herein is not intended to be limited to or by such coaxial conductor configurations.)

At the proximal end (that is, the end that is to be connected to the pacemaker) of such bipolar leads it is common to employ a tip electrode and a ring electrode, each electrode being connected to one of the conductors within the lead. The tip electrode is typically made from a rigid tube having thick or heavy walls. (A channel or hole passing through the center of this thick-wall tip electrode provides a convenient means for introducing a stylet into the lead.) Due to the thickness of the walls of the proximal tip electrode, a firm electrical connection can be made thereto, as well as a firm physical connection (to prevent the electrode from inadvertently becoming disconnected from the pacemaker) by transversely driving a setscrew thereagainst. The setscrew is anchored in a suitable connector block that forms part of the "connector" of the pacemaker. (The "connector" of a pacemaker is that portion designed to receive the pacemaker lead). The connector block has a recess or channel therein into which the tip electrode is inserted. (The recess of the connector block may be thought of as the female component of a conventional connector; and the tip electrode may be thought of as the male component.) The setscrew assures firm electrical contact between the male and female components and physically locks or holds the male/female components together. (The connector block, in turn, is electrically connected to the appropriate pacemaker circuits.) A further description of this type of connection technique, including some of the problems associated therewith, as used with respect to a proximal tip electrode, can be found in U.S. Pat. No. 3,908,668.

In contrast to the rigid, strong thick-wall proximal tip electrode, the proximal ring electrode of a bipolar lead is rather delicate and easily deformed. As its name implies, the ring electrode is a ring. In order to allow the proximal tip conductor and insulation to pass therethrough, the ring electrode by necessity has thin walls. Hence, the proximal ring electrode may be easily deformed or otherwise damaged in setscrew-type connector blocks.

Despite the rather delicate nature of a proximal ring electrode, setscrew-type connector blocks are nonetheless commonly used in the art in order to make electrical contact therewith. In such arrangements, a second connector block (separate or insulated from the first connector block with which the tip electrode makes contact) has a recess or opening therethrough into which the ring electrode is inserted. A second setscrew, threadably engaged with the second connector block, is then screwed against the ring electrode in order to make firm electrical contact therewith. However, great care must be exercised when the set screw is adjusted in order to prevent deformation of the ring electrode. Such deformation could not only render the lead unusable in the future (should the pacemaker have to be subsequently replaced), but it could also render the lead inoperable. For example, the ring could be deformed to the point that the ring does not easily fit within the opening of its connector block, or is tightly wedged therein. In either event, insertion and removal forces could easily exceed those forces for which the lead was designed. In severe cases of ring deformation, the inner conductor could even be shorted to the outer conductor. Inasmuch as it is highly desirable to be able to leave a lead in place within a patient once implanted (so as to reduce any trauma or shock that might accompany insertions and removals of pacing leads into and out of the heart), and therefore to be able to reuse the implanted lead over and over again with as many different pacemakers as may be required, it is important that the integrity of the proximal electrodes be maintained. Hence, there is a need in the art for a pacemaker connector block that can make firm and reliable electrical contact with a proximal ring electrode without subjecting the ring electrode to the risk of deformation or other damage. The present invention is directed to this need.

SUMMARY OF THE INVENTION

The connector block of the present invention includes a recess or channel into which the ring electrode is inserted. A "C" ring is also inserted in the connector block between the ring electrode and an inner wall of the recess or channel of the connector block. A setscrew adjustably forces the C-ring against the ring electrode and distributes the contact forces derived from the setscrew uniformly about that portion of the surface of the ring electrode with which the C-ring makes contact. This distribution of forces on the surface of the ring electrode advantageously minimizes the risk of deforming the ring electrode, and prevents any marring of its surface. Further, the C-ring, as pushed or forced by the set screw, is only permitted to transversely move towards the ring electrode a prescribed amount before the ends of the C-ring engage a mechanical stop. This mechanical stop further prevents the ring electrode from being damaged.

The method of attachment of the present invention includes the steps of inserting the proximal ring electrode into the channel or opening of the connector block, applying a transverse force against a first side of the proximal ring, and physically limiting the amount of the transverse force that is thus applied. Preferably, the transverse force is limited through the use of a force-limiting tool on the application of the transverse force, and by a mechanical stop used in cooperation with a C-ring that limits the transverse movement of the C-ring to a prescribed amount.

In an alternative embodiment of the connector block, the C-ring and setscrew are replaced by a spring-contact device. Such spring-contact device includes a C-ring body to which a plurality of resilient arms or fingers are integrally attached. These arms are configured or shaped such that a portion thereof makes firm electrical contact with the connector block and another portion makes firm electrical contact with any ring electrode inserted into the channel or opening of the connector block. Thus, the amount of transverse force applied to the C-ring electrode is set by the spring constant of the material from which the resilient arms or fingers are made. Hence, by design, the force can be limited to a prescribed amount, which force is selected to be sufficient to make firm electrical contact but is insufficient to cause deformation or damage.

BRIEF DESCRIPTION OF THE DRAWINGS

The above and other features of the invention will be more apparent from the following more particular description thereof presented in conjunction with the following drawings wherein:

FIG. 4b is a end view of FIG. 4a;

FIG. 5b is an end view of FIG. 5a.

DETAILED DESCRIPTION OF THE INVENTION

The present invention is best understood with reference to the drawings wherein like numerals will be used to refer to like parts throughout.

Figure 1:
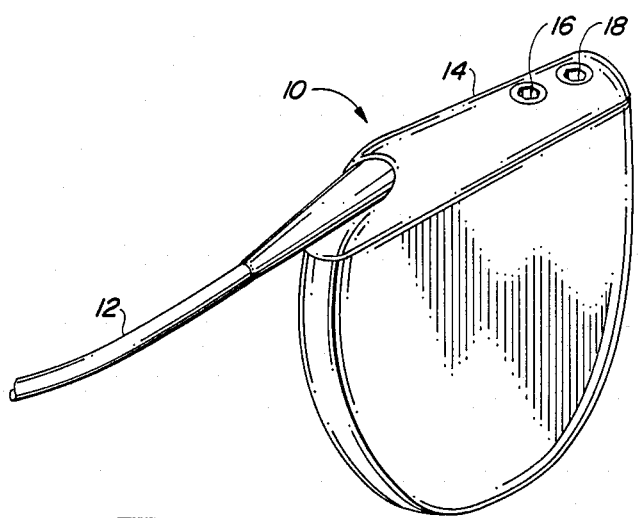
FIG. 1 is a perspective view of a pacemaker having a pacing lead attached thereto.
Figure 3:
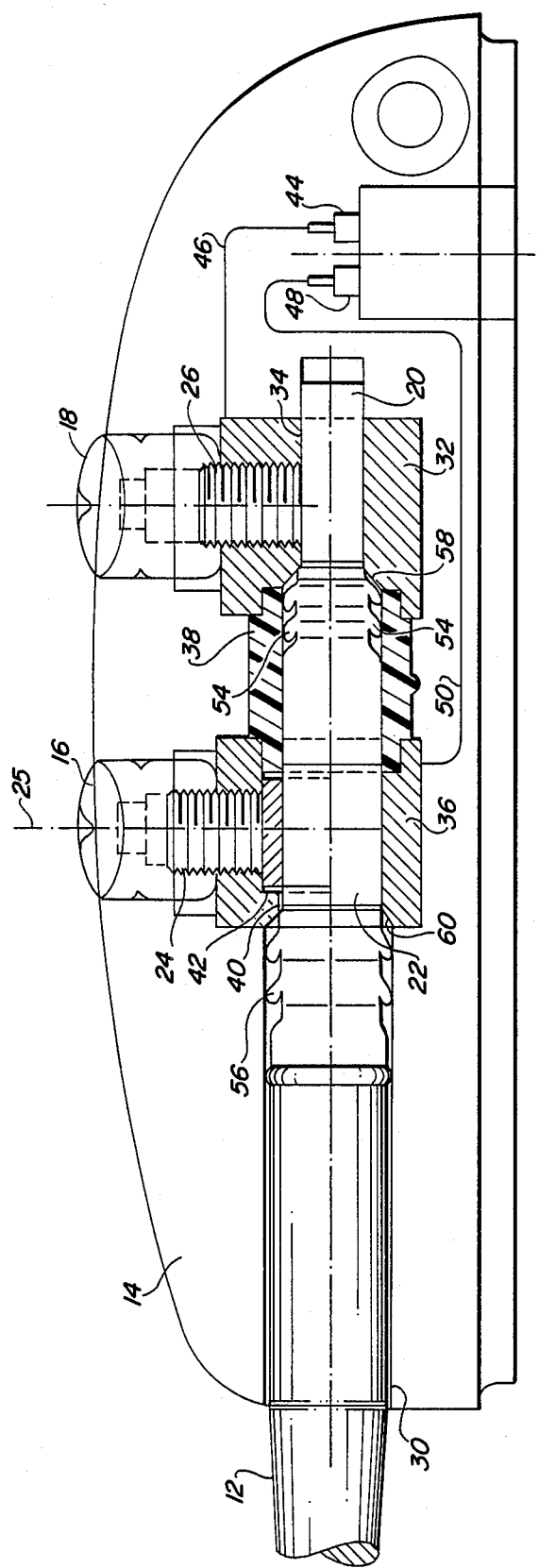
FIG. 3 is a side sectional view of a pacemaker connector with a lead inserted thereinto, and illustrates a connector block in accordance with the present invention.

Referring first to FIG. 1, there is shown a perspective view of a pacemaker 10 having a bipolar pacing lead 12 attached thereto. The lead 12 is inserted into an opening in the connector 14 of the pacemaker. The connector 14, as will be more apparent from the description of FIG. 3 presented below, is that portion of the pacemaker to which a pacer lead 12 can be detachably connected. Typically, two setscrews, accessible through self-sealing septums 16 and 18, are used to securely attach the proximal electrodes of the lead 12 to the appropriate connector blocks within the connector 14.

Figure 2A:
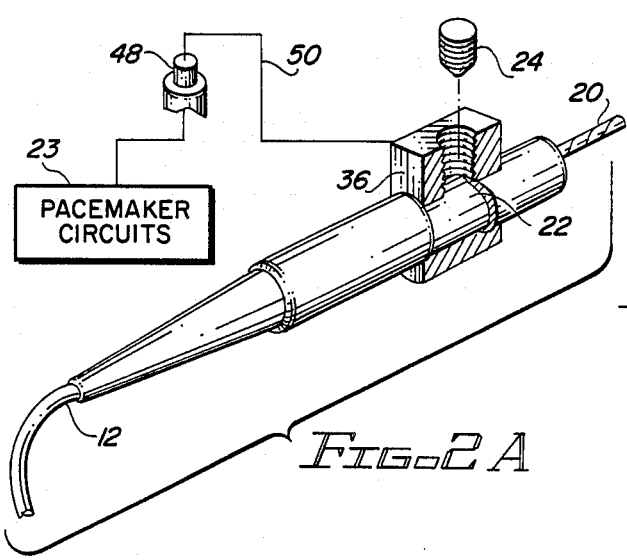
FIG. 2a is a partial perspective view as in FIG. 1, showing those elements used in the prior art to contact and secure the proximal ring electrode of a bipolar lead.

In FIG. 2a, a partial perspective view as in FIG. 1 is shown. However, in FIG. 2a only those elements responsible for making electrical contact with a proximal ring electrode of the lead 12 are shown. In FIG. 2a, the proximal tip electrode 20 and the proximal ring electrode 22, and the connector block 36 (shown with a portion cutaway), can be seen. Also shown is a feedthrough terminal 48 (discussed below in connection with FIG. 3) to which the connector block 36 is electrically connected. In turn, the feedthrough terminal 48 is electrically connected to the pacemaker circuits 23. (This connection is typically made to the reference potential of the circuits 23.)

Figure 2B:
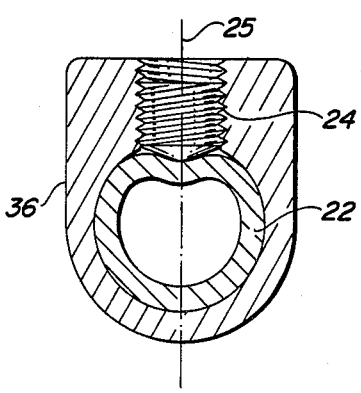
FIG. 2b is an end view of the elements of FIG. 2a illustrating how a proximal ring electrode can easily be deformed by overtightening of the setscrew, which deformation causes the ring electrode to swell within the respective connector block.

As mentioned previously, the tip electrode 20 is typically made from a relatively thick-wall material and is therefore not easily deformed. However, the ring electrode 22 can easily be damaged or deformed by a setscrew 24 that is tightened thereagainst. A common type of deformation is illustrated in FIG. 2b wherein the set screw 24, when urged along its movement axis 25, causes the ring electrode 22 to cave in, thus damaging the electrode and possibly preventing its normal extraction from, and subsequent insertion into, a connector block.

Referring next to FIG. 3, a side sectional view of the connector 14 of the pacemaker is shown. The bipolar lead 12 is inserted into a receiving channel 30 formed within the connector 14. A first connector block 32 is positioned at the end of this channel 30. This first connector block 32 has a recess or channel 34 therethrough adapted to receive the tip electrode 20.

Spaced apart from the first connector block 32 is a second connector block 36. A non-conductive tie-together tube 38 physically ties the connector block 32 to the connector block 36. This tube 38 also accurately aligns the channel 34 of the first connector block 36 to a channel or recess 40 of the second connector block 36. The proximal ring electrode 22 is inserted into the channel 40 in order to engage the connector block 36.

The lead 12 is secured to the connector blocks 32 and 36 with setscrews 26 and 24. Setscrew 26 is threadably coupled to the connector block 32 and makes contact with the tip electrode 20. Setscrew 24 is threadably coupled to the connector block 36 and makes contact with the proximal ring electrode 22 through a C-ring 42 (described below). Septums 16 and 18 provide a covering for the setscrews 24 and 26. A special tool (not shown), such as a torque-limiting Allen wrench, can be punctured through the septums 18 and 16 in order to engage and tighten the set screws 26 and 24 respectively, as is known in the art.

Connector block 32 is electrically coupled to feedthrough terminal 44 by a suitable connection means, such as conducting line 46. Similarly, connector block 36 is electrically coupled to feedthrough terminal 48 by means of a suitable connection means, such as conducting line 50. In turn, the appropriate circuits of the pacemaker 10 are electrically connected with the feedthrough terminals 44 and 48, thereby allowing the connector blocks 32 and 36 to be electrically connected to the circuits of the pacemaker.

Figure 4A:
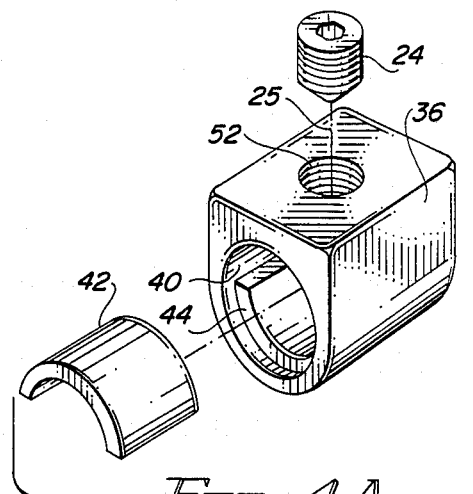
FIG. 4a is a perspective view of a connector block in accordance with one embodiment of the present invention.
Figure 4B:
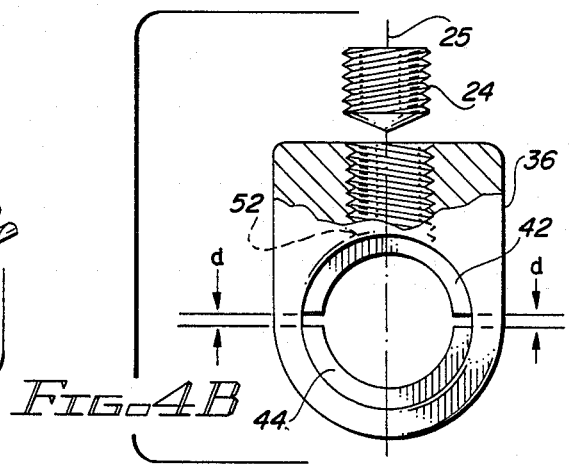

Referring next to FIGS. 4a and 4b, a perspective and end view respectively of the connector block 36 is shown. As indicated in FIG. 4a, the connector block 36 has a channel (or recess) 40 passing therethrough. A second opening 52, threaded to receive the setscrew 24, is placed in the connector block 36 so as to be substantially transverse or orthogonal to the opening or recess 40. A partial or half sleeve, such as a C-ring 42, is inserted into the channel 40 so as to block the opening 52 as it opens into the channel 40. A second C-ring 44, or equivalent, is affixed or placed inside of the channel 40 so as to be below the first C-ring 42, as best shown in FIG. 4b. The purpose of this second C-ring 44, is to act as a seat against which the proximal ring electrode 22, is forced and also to hold the first C-ring 42 in its proper radial position.

The C-ring 42 and the C-ring 44 are sized such that when inserted into the channel 40 of the connector block 36 and fully pressed against the interior wall of the channel 40, a space or distance "d" exists between the respective ends thereof. (See FIG. 4b.) Because the C-ring 44 remains permanently affixed within or integrally part of the channel 40, whereas the C-ring 42 is not, the C-ring 42 may move transversely (along the axis 25) the distance "d" before being stopped by the ends of the C-ring 44. Thus, the C-ring 44 functions as a mechanical stop to limit the distance that the C-ring 42 may move when pushed by the setscrew 24. This distance "d" is designed to be sufficiently long to allow a firm grip on the proximal ring electrode 22, yet sufficiently short to prevent the ring electrode 22 from being deformed.

In the preferred embodiment, the ring electrode 22 has an outside diameter of 0.105 inches. The C-ring 42 has an inside diameter that substantially matches this outside diameter of the ring electrode. Further, the C-ring 42 has a thickness of approximately 0.020 inches. The distance "d" (FIG. 4b) is approximately 0.003 inches. The connector block 36, the C-ring 42, and the setscrew 24 are all made from 316L stainless steel alloy, a conductive metal that is safe to use in the presence of body fluids and that is compatable from a Galvanic corrosion standpoint with existing lead materials. The connector blocks 32 and 36, including the tie-together tube 38, are all placed within the connector 14 in accordance with techniques known in the art. (The connector 14 is a cast or molded part that is realized with a suitable two component epoxy resin.)

In order to connect the lead 12 to the pacemaker 10, the following technique is used. First, the proximal end of the lead 12 is pushed into the channel 30 of the connector 14. Resilient elastomer ribs 54 selectively placed near the tip electrode 20, and similar ribs 56 placed near the ring electrode 22, provide a snug sealed fit and further engage shoulders 58 and/or 60 of the channel 30 in order to prevent further insertion of the lead 12 when it has been fully inserted into the channel 30. Once thus inserted, a suitable torque limiting tool is inserted through the septum 18 in order to engage the set screw 26. This set screw 26 is suitably tightened in order to firmly engage the tip electrode 20. The same tool is then inserted through the septum 16 in order to engage the set screw 24. This set screw is turned until the tool indicates a tight condition.

It is noted that for the embodiment of FIGS. 4a and 4b, that a second C-ring 44, or equivalent, is permanently affixed in the bottom of the channel 40 of the connector block 36. The purpose of this second C-ring 44 is to provide a mechanical stop against which the ends of the C-ring 42 engage when the C-ring 42 has traveled the maximum allowable distance "d" in the direction of axis 25 (as it grips the ring electrode 22). Any suitable stop means could, of course, be used in order to realize this stop function. For example, as a casting or otherwise molded part, the connector block 36 could have the C-ring 44 as an integral part thereof. Because the connector block 36 lends itself well to being fabricated by the investment casting process, the preferred manner of construction is to make the equivalent of the C-ring 44 as an integral part of the connector block 36.

Figure 5A:
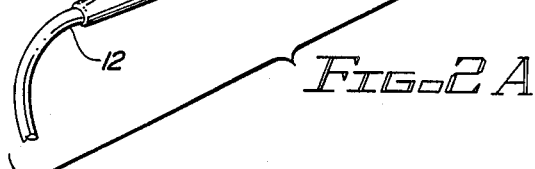
FIG. 5a is a perspective view of a connector block in accordance with an alternative embodiment of the present invention.
Figure 5A:
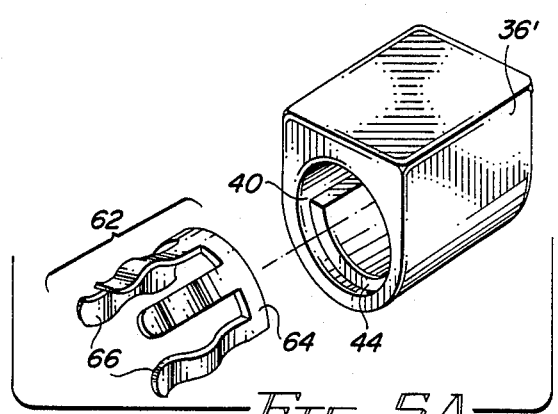
Figure 5B:
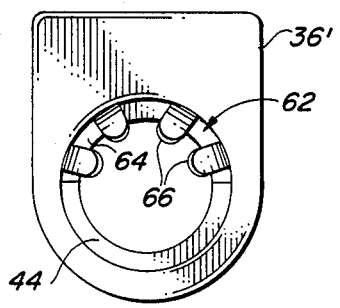

Referring next to FIGS. 5a and 5b, an alternative embodiment of the present invention is shown. In accordance with this alternative embodiment, a connector block 36' is employed having a channel 40 therethrough and a C-ring 44, or equivalent affixed to or molded as part of the bottom of the channel 40. However, unlike the embodiment shown in FIG. 4a, the embodiment of FIG. 5a does not use a set screw. Rather, a spring-contact device 62 is inserted into that portion of the channel 40 that is occupied by the C-ring 42 in FIG. 4a. The spring-contact device 62 includes a C-ring body portion 64 to which a plurality of resilient arms or fingers 66 are attached. These resilient arms 66 are configured or shaped so as to assure electrical contact both with the connecting block 36' and with any ring electrode inserted into the channel 40. That is, as best seen in FIG. 5b, the arms 66 protrude into the channel 40 a sufficient distance to insure contact with the ring electrode 22. Because these arms 66 are resilient, they will exert a force against the ring electrode 22 as a function of the spring constant of the material from which they are made. This material and associated spring constant can be selected so that the force is sufficient to maintain firm electrical contact with any ring electrode yet not sufficient to cause damage (deformation) to any ring-electrode. A suitable spring contact device 62 can be made from 316L stainless steel alloy having a thickness of from 0.004 to 0.008 inches.

The preceeding description is of the best presently contemplated mode of carrying out the invention. This description is not to be taken in a limiting sense but is made mainly for the purpose of describing the general principles of the invention. The scope of the invention should be determined with reference to the appended claims.

What is claimed is:

1. A pacemaker connector block assembly for use with an implantable pacemaker and an implantable bipolar pacemaker lead; said bipolar pacemaker lead having a proximal end that includes at least two spaced-apart electrodes, a first of which is substantially non-deformable when subjected to a holding force, and a second of which is easily deformable when subjected to a holding force of the same magnitude as that applied to the first electrode, said pacemaker having electrical circuits therein to which the first and second proximal electrodes are to be electrically connected, said connector block assembly comprising:
  a receiving channel for receiving the proximal end of said bipolar pacemaker lead, including said first and second spaced-apart electrodes;
  first contact means within said receiving channel for applying a first holding force to said first electrode and for maintaining electrical contact therewith;
  second contact means within said receiving channel for applying a second holding force to said second electrode and for maintaining electrical contact therewith, said second contact means including force limiting means internal to said connector block assembly for limiting the amount of the second holding force that can be applied to said second electrode to a value that prevents deformation of said second electrode;
  means for electrically connecting said first and second contact means with the electrical circuits within said pacemaker; and
  sealing means for preventing body fluids from contacting said first and second contact means when the proximal end of said bipolar pacemaker lead is inserted into said receiving channel;
  whereby the proximal end of said bipolar pacing lead may be removably and sealably inserted into said connector block assembly.

2. The pacemaker connector block assembly of claim 1 wherein said force limiting means of said second contact means comprises resilient conductive fingers in electrical contact with an inside wall of said channel, said fingers being configured to firmly push against the second electrode whenever said second electrode is inserted into said receiving channel, and wherein said first contact means comprises a setscrew threadably inserted into said connector block, a tip of said setscrew protruding out progressively further from an inside wall of said receiving channel as said setscrew is rotated in a first direction, said protruding tip contacting said first electrode of said bipolar pacemaker lead and making firm contact therewith.

3. The pacemaker connector block assembly of claim 1 wherein said second contact means comprises:

a C-ring inserted into the channel of said connector block so as to partially wrap around and evenly contact the second electrode of the proximal end of said bipolar pacemaker lead, said C-ring lying between said second electrode and an inside wall of said receiving channel;

means for applying a transverse force to said C-ring so as to force and maintain said C-ring tightly against the second electrode of the proximal end of said pacemaker lead, whereby the second electrode of the proximal end of said pacemaker lead is firmly gripped between said C-ring and the inside wall of said connector block.

4. The pacemaker connector block assembly of claim 3 wherein said force limiting means includes a physical stop within said receiving channel that engages the ends of said C-ring whenever said C-ring has transversely moved against said second electrode a prescribed linear distance, the further transverse linear movement of said C-ring being stopped once engagement of the C-ring ends with said stop has occurred; whereby deformation of the second electrode of the bipolar pacemaker lead, which deformation would result from excessive transverse linear movement of said C-ring, is prevented.

5. The pacemaker connector block assembly of claim 4 wherein said first and second contact means each comprise a setscrew threadably inserted into said connector block, a tip of said setscrew protruding out progressively further from the inside wall of said channel as said setscrew is rotated in a first direction, said protruding tip of the setscrew of said first contact means contacting said first electrode of said bipolar pacemaker lead and making firm contact therewith, said protruding tip of the setscrew of said second contact means contacting said C-ring and causing said C-ring to transversely move against the second electrode of said bipolar pacemaker lead, said C-ring serving to distribute the force applied to the C-ring at the tip of said setscrew over the entire surface area of said second electrode in contact with said C-ring.

* * * * *